United States Patent [19]
Michelotti et al.

[11] Patent Number: 5,929,098
[45] Date of Patent: Jul. 27, 1999

[54] FUNGICIDICALLY ACTIVE N-ACETONYLBENZAMIDE COMPOUNDS

[75] Inventors: Enrique Luis Michelotti, Fort Washington; David Hamilton Young, Ambler, both of Pa.

[73] Assignee: Rohm and Haas Company, Philadelphia, Pa.

[21] Appl. No.: 08/877,939

[22] Filed: Jun. 18, 1997

Related U.S. Application Data

[60] Provisional application No. 60/020,517, Jun. 28, 1996.

[51] Int. Cl.$^6$ ..................... C07C 331/12; C07D 213/02; A01N 47/46; A01N 43/40
[52] U.S. Cl. ..................... 514/352; 546/310; 564/163; 514/619
[58] Field of Search ..................... 546/310; 564/163; 514/357, 619

[56] References Cited

U.S. PATENT DOCUMENTS

| | | | |
|---|---|---|---|
| 3,661,991 | 5/1972 | McNulty et al. | 514/622 |
| 3,751,239 | 8/1973 | McNulty et al. | 71/118 |
| 4,822,902 | 4/1989 | Carley et al. | 558/14 |
| 4,863,940 | 9/1989 | Sharma | 514/359 |
| 5,075,471 | 12/1991 | Michelotti et al. | 556/144 |
| 5,254,584 | 10/1993 | Michelotti et al. | 514/514 |
| 5,304,572 | 4/1994 | Michelotti et al. | 514/514 |
| 5,453,531 | 9/1995 | Seitz et al. | 560/29 |
| 5,514,719 | 5/1996 | LaTorse et al. | 514/622 |

FOREIGN PATENT DOCUMENTS 1643945  3/1972  Germany .

*Primary Examiner*—Zinna Northington Davis
*Attorney, Agent, or Firm*—Guy T. Donatiello

[57] ABSTRACT

Novel N-acetonylbenzamides are disclosed. These compounds are useful in controlling phytopathogenic fungi.

11 Claims, No Drawings

FUNGICIDICALLY ACTIVE N-ACETONYLBENZAMIDE COMPOUNDS

This application is a based on Provisional Application No. 60/020,517 filed Jun. 28, 1996.

The present invention regards certain N-acetonylbenzamide compounds that are fungicidally active.

It is known that benzamides of the class of N-(1,1-dialkyl-3-chloroacetonyl) substituted benzamides exhibit fungicidal activity, see, e.g. U.S. Pat. Nos. 3,661,991 and 3,751,239. While the compounds disclosed in U.S. Pat. Nos. 5,254,584 and 5,304,572 exhibit a favorable balance of fungicidal activity and phytotoxicity, there is a continuing interest in the discovery of new fungicidal compounds.

The N-acetonylbenzamide compounds of the present invention are those of the structural Formula 1:

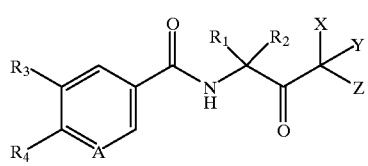

wherein:

A is N or C—$R_5$;

$R_1$ and $R_2$ are each independently H, $(C_1-C_6)$alkyl, halo$(C_1-C_6)$alkyl, $(C_2-C_6)$alkenyl, or $(C_2-C_6)$alkynyl, provided that at least one of $R_1$ and $R_2$ is not H;

$R_3$, $R_4$ and $R_5$ are each independently H, halo, cyano, $(C_1-C_6)$alkyl, halo$(C_1-C_6)$alkyl, $(C_2-C_6)$alkenyl, $(C_2-C_6)$alkynyl, $(C_1-C_6)$alkoxyl, halo$(C_1-C_6)$alkoxyl, nitro, carboxyl, —$NR_6R_7$, —$CR_8$=$NOR_9$, $NHCOOR_8$, or —$CONR_{10}R_{11}$, provided that at least one of $R_3$, $R_4$, and $R_5$ is —$NR_6R_7$;

$R_6$ and $R_7$ are each independently H, $(C_1-C_6)$alkyl, or $(C_1-C_6)$alkylcarbonyl;

$R_8$ is H, $(C_1-C_6)$alkyl, $(C_2-C_6)$alkenyl, $(C_2-C_6)$alkynyl, $(C_1-C_6)$alkylcarbonyl$(C_1-C_4)$alkyl;

$R_9$ is H, $(C_1-C_6)$alkyl, $(C_2-C_6)$alkenyl, $(C_2-C_6)$alkynyl, or $(C_1-C_4)$alkylcarbonyl;

$R_{10}$ and $R_{11}$ are each independently H, $(C_1-C_6)$alkyl, $(C_2-C_6)$alkenyl, or $(C_2-C_6)$alkynyl;

X, Y and Z are each independently H, halo, cyano, thiocyano, isothiocyano or $(C_1-C_6)$alkylsulfonyloxy, provided that at least one of X, Y and Z is halo, cyano, thiocyano, isothiocyano, or $(C_1-C_6)$alkylsulfonyloxy;

and agronomically acceptable salts thereof.

The present invention also includes the entiamers, metal salts and complexes of Formula 1.

The term "halo" means fluoro, chloro, bromo or iodo.

The term "$(C_1-C_6)$alkyl" means a straight or branched alkyl group having from 1 to 6 carbons per group, and includes, e.g, methyl, ethyl, n-propyl, isopropyl, n-butyl, isobutyl, t-butyl, pentyl and hexyl. The alkyl group may also be substituted with from 1 to 5 halogen atoms, and includes, e.g, chloromethyl, trifluoromethyl, bromoethyl, 1,1,1,2,2-pentafluoroethyl, iodopropyl, chlorobutylbutyl.

The term "$(C_2-C_6)$alkenyl" means a straight or branched group having from 2 to 6 carbons per group, and includes, e.g, ethenyl, 2-propenyl, n-butyl, 2-butenyl and 2-methyl-2-propenyl.

The term "$(C_2-C_6)$alkynyl" means a straight or branched alkynyl group having from 2 to 6 carbons per group, and includes, e.g, ethynyl, 2-propynyl and 2-butynyl.

The term "$(C_1-C_6)$alkoxyl" means a straight or branched alkoxyl group having from 1 to 4 carbons per group, and includes, e.g, methoxyl, propoxyl, n-butoxyl and t-butoxyl.

The term "$(C_1-C_6)$alkylcarbonyl" includes, e.g. methylcarbonyl, butylcarbonyl.

The term "$(C_1-C_6)$alkylsulfonyloxy" includes, e.g. methylsulfonyloxy and propylsulfonyloxy.

The term "$(C_1-C_6)$alkylcarbonyl$(C_1-C_4)$alkyl" includes, for example, methylcarbonyloxymethyl, methylcarbonyloxyethyl, methylcarbonyloxypropyl, methylcarbonyloxybutyl, ethylcarbonyloxymethyl, ethylcarbonyloxyethyl, ethylcarbonyloxypropyl, ethylcarbonyloxybutyl, propylcarbonyloxyethyl, propylcarbonyloxypropyl, butylcarbonyloxyethyl and butylcarbonyloxybutyl.

Suitable —$NR_6R_7$ substituents include amido, monosubstituted amino and disubstituted amino such as, e.g., amino, methylamino, ethylamino, carboxymethylamino and diethylamino.

The term "carboxyl" means a group having the structural formula —COOH.

The term "nitro" means a group having the structural formula —$NO_2$.

The term "cyano" means a group having the structural formula —CN.

The term "thiocyano" means a group having the structural formula —SCN.

The term "isothiocyano" means a group having the structural formula —NCS.

Suitable —$CR_8$=$NOR_9$ substituents includes, e.g., hydroximinomethyl, methoxyiminomethyl, ethoxyiminomethyl, methoxyiminoethyl, dimethoxyiminomethyl and methylcarbonyliminomethyl.

Suitable —$CONR_{10}R_{11}$ substituents include amido, monosubstituted amido and disubstituted amido such as, e.g., amido, methylamido, dimethylamido, propylamido, dibutylamido.

The term "agrochemically acceptable salt" includes, e.g., metal salts such as sodium, calcium and magnesium salts, ammonium salts such as isopropylammonium salts and trialkylsulfonium salts such as trimethylsulfonium salts.

Compounds according to the present invention include, for example:

N-(3-chloro-1-ethyl-1-methyl-2-oxopropyl)-4-amino-3-chloro-5-nitrobenzamide,

N-(3-chloro-1-ethyl-1-methyl-2-oxopropyl)-4-amino-3-chloro-5-phenylbenzamide,

N-(3-chloro-1-ethyl-1-methyl-2-oxopropyl)-4-amino-3-chloro-5-vinylbenzamide,

N-(3-chloro-1-ethyl-1-methyl-2-oxopropyl)-4-amino-3-chloro-5-ethynylbenzamide,

N-(3-chloro-1-ethyl-1-methyl-2-oxopropyl)-4-amino-3-chloro-5-chloromethylbenzamide, N-(3-chloro-1-ethyl-1-methyl-2-oxopropyl)-4-amino-3-chloro-5-bromomethylbenzamide, N-(3-chloro-1-ethyl-1-methyl-2-oxopropyl)-4-amino-3-chloro-5-chloroethylbenzamide, N-(3-chloro-1-ethyl-1-methyl-2-oxopropyl)-4-amino-3-chloro-5-methoxycarbonyllbenzamide, N-(3-chloro-1-ethyl-1-methyl-2-oxopropyl)-4-amino-3-chloro-5-cyanobenzamide, N-(3-chloro-1-ethyl-1-methyl-2-oxopropyl)-4-amino-3-chloro-5-methylbenzamide, N-(3-chloro-1-ethyl-1-methyl-2-oxopropyl)-3-amino-4-chloro-5-cyanobenzamide, N-(3-chloro-1-ethyl-1-methyl-2-oxopropyl)-3-amino-5-chloro-4-cyanobenzamide, N-(3-chloro-1-ethyl-1-methyl-2-oxopropyl)-3-amino-4-chloro-5-nitrobenzamide,
N-(3-chloro-1-ethyl-1-methyl-2-oxopropyl)-3-amino-5-chloro-4-nitrobenzamide,
N-(3-chloro-1-ethyl-1-methyl-2-oxopropyl)-3-amino-5-bromo-4-chlorobenzamide,
N-(3-chloro-1-ethyl-1-methyl-2-oxopropyl)-3,4-diamino-5-chlorobenzamide,
N-(3-chloro-1-ethyl-1-methyl-2-oxopropyl)-3,4-diamino-5-nitrobenzamide,
N-(3-chloro-1-ethyl-1-methyl-2-oxopropyl)-3,4-diamino-5-methylbenzamide,
N-(3-chloro-1-ethyl-1-methyl-2-oxopropyl)-3,4-diamino-5-cyanobenzamide,
N-(3-chloro-1-ethyl-1-methyl-2-oxopropyl)-4-amino-3,5-difluorobenzamide,
N-(3-chloro-1-ethyl-1-methyl-2-oxopropyl)-4-acetamido-3,5-dichlorobenzamide,
N-(3-chloro-1-ethyl-1-methyl-2-oxopropyl)-4-methylamino-3,5-dichlorobenzamide,
N-(3-chloro-1-ethyl-1-methyl-2-oxopropyl)-4-dimethylamino-3,5-dichlorobenzamide,
N-(3-chloro-1-ethyl-1-methyl-2-oxopropyl)-4-amino-3-methoxyiminomethyl-5-methylbenzamide,
N-(3-chloro-1-ethyl-1-methyl-2-oxopropyl)-4-amino-3-bromo-5-methoxyiminomethylbenzamide,
N-(3-cyano-1-ethyl-1-methyl-2-oxopropyl)-4-amino-3,5-dichlorobenzamide,
N-(3-thiocyano-1-ethyl-1-methyl-2-oxopropyl)-4-amino-3,5-dichlorobenzamide,
N-(3-isothiocyano-1-ethyl-1-methyl-2-oxopropyl)-4-amino-3,5-dichlorobenzamide,
N-(3-chloro-1-ethyl-1-methyl-2-oxopropyl)-3-amino-5-chlorobenzamide,
N-(3-chloro-1-ethyl-1-methyl-2-oxopropyl)-3-amino-5-nitrobenzamide,
N-(3-chloro-1-ethyl-1-methyl-2-oxopropyl)-3-amino-5-cyanobenzamide,
N-(3-chloro-1-ethyl-1-methyl-2-oxopropyl)-3-amino-5-methylbenzamide,
N-(3-chloro-1-ethyl-1-methyl-2-oxopropyl)-3-amino-5-methoxyiminomethylbenzamide,
N-(3-chloro-1-ethyl-1-methyl-2-oxopropyl)-3-amino-5-methoxyiminomethylbenzamide,
N-(3-chloro-1-ethyl-1-methyl-2-oxopropyl)-3-amino-5-chloro-4-methoxyiminomethylbenzamide,
N-(3,3-dichloro-1-ethyl-1-methyl-2-oxopropyl)-4-amino-3-bromo-5-methoxyiminomethylbenzamide,
N-(3,3-dichloro-1-ethyl-1-methyl-2-oxopropyl)-4-amino-3-bromo-5-methoxyiminomethylbenzamide,
N-(3,3-dibromo-1-ethyl-1-methyl-2-oxopropyl)-4-amino-3-chloro-5-methoxyiminomethylbenzamide,
N-(3-bromo-1-ethyl-1-methyl-2-oxopropyl)-4-amino-3-bromo-5-methoxyiminomethylbenzamide,
N-(3-bromo-1-ethyl-1-methyl-2-oxopropyl)-4-amino-3-chloro-5-methoxyiminomethylbenzamide,
N-(3,3-dibromo-1-ethyl-1-methyl-2-oxopropyl)-4-amino-3-chloro-5-methoxyiminomethylbenzamide,
N-(3-iodo-1-ethyl-1-methyl-2-oxopropyl)-4-amino-3-chloro-5-methoxyiminomethylbenzamide,
N-(3-fluoro-1-ethyl-1-methyl-2-oxopropyl)-4-amino-3-chloro-5-methoxyiminomethylbenzamide,
N-(3-fluoro-3-iodo-1-ethyl-1-methyl-2-oxopropyl)-4-amino-3-chloro-5-methoxyiminomethylbenzamide,
N-(3-chloro-3-fluoro-1-ethyl-1-methyl-2-oxopropyl)-4-amino-3-chloro-5-methoxyiminomethylbenzamide,
N-(3-bromo-3-fluoro-1-ethyl-1-methyl-2-oxopropyl)-4-amino-3-chloro-5-methoxyiminomethylbenzamide,
N-(3-cyano-1-ethyl-1-methyl-2-oxopropyl)-4-amino-3-chloro-5-methoxyiminomethylbenzamide,
N-(3-thiocyano-1-ethyl-1-methyl-2-oxopropyl)-4-amino-3-chloro-5-methoxyiminomethylbenzamide,
N-(3-isothiocyano-1-ethyl-1-methyl-2-oxopropyl)-4-amino-3-chloro-5-methoxyiminomethylbenzamide,
N-(3-chloro-3-fluoro-1-ethyl-1-methyl-2-oxopropyl)-4-amino-3,5-dichlorobenzamide,
N-(3-chloro-3-iodo-1-ethyl-1-methyl-2-oxopropyl)-4-amino-3,5-dichlorobenzamide,
N-(3-bromo-3-chloro-1-ethyl-1-methyl-2-oxopropyl)-4-amino-3,5-dichlorobenzamide,
N-(3,3-dibromo-1-ethyl-1-methyl-2-oxopropyl)-4-amino-3,5-dichlorobenzamide,
N-(3-bromo-3-fluoro-1-ethyl-1-methyl-2-oxopropyl)4-amino-3,5-dichlorobenzamide,
N-(3-bromo-3-iodo-1-ethyl-1-methyl-2-oxopropyl)-4-amino-3,5-dichlorobenzamide and
N-(3-bromo-1-ethyl-1-methyl-2-oxopropyl)-4-amino-3,5-dichlorobenzamide.
N-(3-chloro-1-ethyl-1-methyl-2-oxopropyl)-6-amino-5-methoxyiminomethylnicotinamide hydrochloride
(N-(3-chloro-1-ethyl-1-methyl-2-oxopropyl)-6-amino-5-methoxyiminomethylnicotinamide
(N-(3-chloro-1-ethyl-1-methyl-2-oxopropyl)-5-amino-6-methoxyiminomethylnicotinamide
(N-(3-chloro-1-ethyl-1-methyl-2-oxopropyl)-5-amino-6-methoxyiminomethylnicotinamide hydrochloride.

In a preferred embodiment, $R_1$ and $R_2$ are each independently ($C_1$–$C_6$)alkyl. More preferably, $R_1$ is methyl and $R_2$ is ethyl.

In a preferred embodiment, $R_3$, $R_4$ and $R_5$ are each independently H, CH=NOCH$_3$, ($C_1$–$C_6$)alkyl, halo, nitro, cyano or —NR$_6$R$_7$, provided that at least one of $R_3$, $R_4$ and $R_5$ is NR$_6$R$_7$, and wherein $R_6$ and $R_7$ are each independently H or ($C_1$–$C_6$)alkyl. More preferably, $R_6$ and $R_7$ are each H.

In a preferred embodiment, X, Y and Z are each independently H, halo, cyano, thiocyano or isothiocyano, provided that at least one of X, Y and Z is halo, cyano, thiocyano or isothiocyano. More preferably, X and Y are each H and Z is halo. Even more preferably, X and Y are each H and Z is chloro.

In a highly preferred embodiment, A is —CR$_5$, $R_1$ is methyl, $R_2$ is ethyl, $R_3$ and $R_5$ are each ($C_1$–$C_6$)alkyl, halo, CH=NOCH$_3$ or nitro, $R_4$ is NH$_2$, X and Y are each H and Z is chloro.

In an alternative highly preferred embodiment, A is N, $R_1$ is methyl, $R_2$ is ethyl, $R_3$ is H, ($C_1$–$C_6$)alkyl, halo, CH=NOCH$_3$ or nitro, $R_4$ is —NH$_2$, X and Y are each H and Z is chloro.

The compounds of the present invention are prepared, for example, by a four-step process (Scheme A) set forth below:

SCHEME A

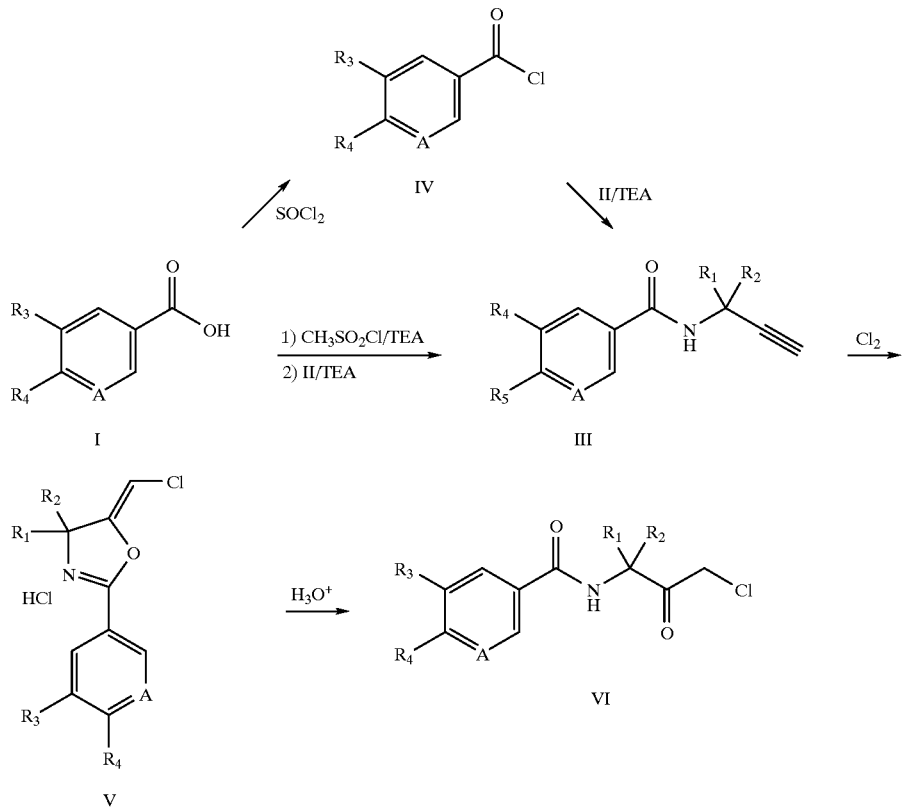

The starting substituted benzoic acid of Formula I:

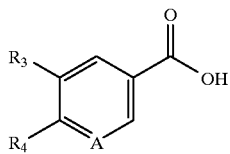

I wherein A, $R_3$, and $R_4$ are as defined as above in Formula 1, is reacted with approximately one equivalent of methanesulfonyl chloride in the presence of a base, such as triethylamine (TEA), using tetrahydrofuran or ethyl ether, alone or combined with dimethylformamide as solvent at $-20°$ C., followed by addition of the corresponding substituted propargylamine hydrochloride of Formula II:

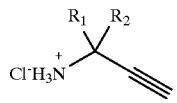

II and triethylamine yielding the expected N-substituted benzamide of Formula III above.

The resulting acetylenic amides of Formula III are treated with halogen or a halogen source at a temperature of $-78°$ C. to $-10°$ C. in the presence of a solvent, such as methylene chloride or chloroform or a mixture of chloroform and hexane to give the intermediate oxazoline hydrochlorides of Formula V, which are readily hydrolyzed under acidic conditions using hydrochloric acid or sulfuric acid in a solvent such as methanol or tetrahydrofuran at a temperature of $40°$ C. to $60°$ C. yielding the N-acetonylbenzamides of Formula VI.

In certain cases the amino group can be introduced by catalytic hydrogenation of N-acetonylnitrobenzamides (Formula VI, $R_3$ or $R_4$=$NO_2$), as shown in Scheme B.

Scheme B

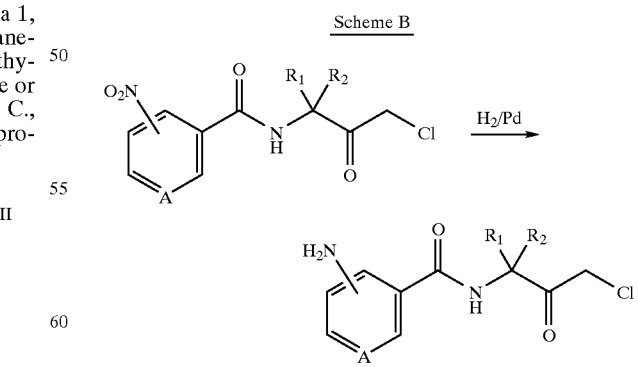

Alternatively, compounds of Formula VI can be prepared by treating the corresponding aromatic benzoic acid with methanesulfonyl chloride followed by addition of 3,3-dichloro-2-keto-1,1-disubstituted propylamines VII:

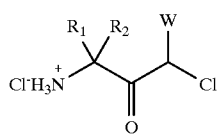

VII W = Cl
VIIa W = H in the presence of a base such as triethylamine and a solvent such as methylene chloride yielding the intermediate N-dichloroacetonylbenzamides of Formula VIII, which by treatment with hydrogen and a catalyst in the presence of a solvent such as ethanol yielded the expected acetonylbenzamides of Formula VI. (Scheme C)

SCHEME C

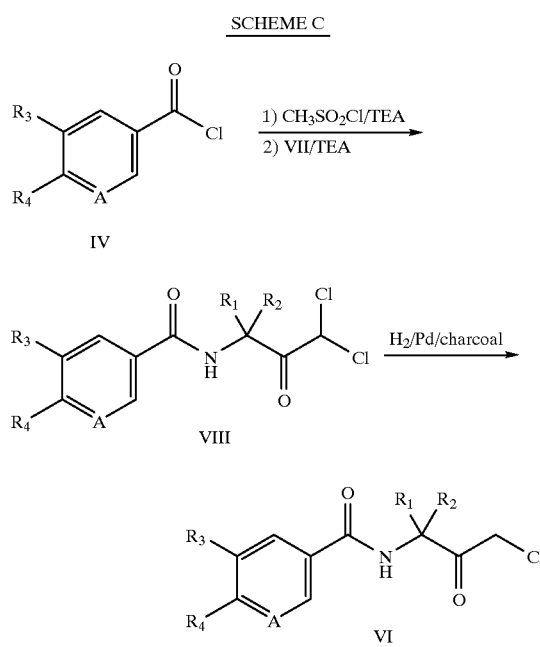

SCHEME C

Alternatively selective catalytic dehalogenation of VII, by treatment with hydrogen in the presence of a catalyst such as palladium, yields the corresponding a-amino-a'-chloroketone VIIa, which by reaction with the corresponding acyl chloride yields the expected N-acetonylbenzamide VI.

The starting benzoic acids are either commercially available or can be prepared by procedures known in the literature. The benzoic acid precursor of compound 3 can be prepared as indicated below in Scheme D.

Scheme D

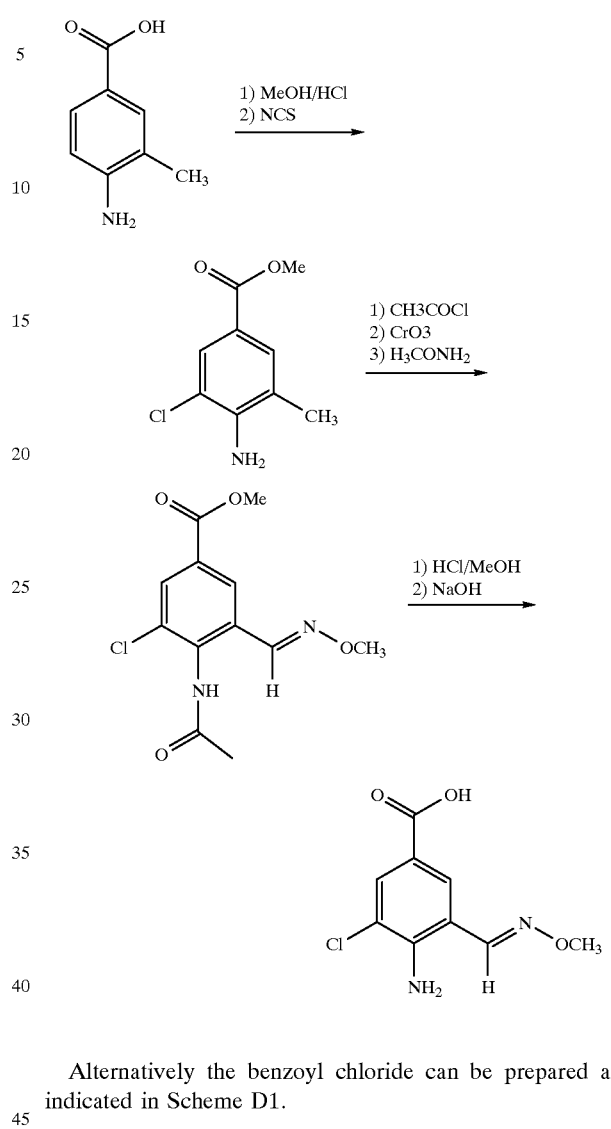

Alternatively the benzoyl chloride can be prepared as indicated in Scheme D1.

Scheme D1

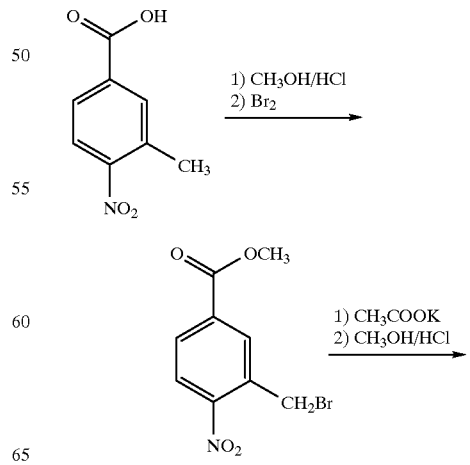

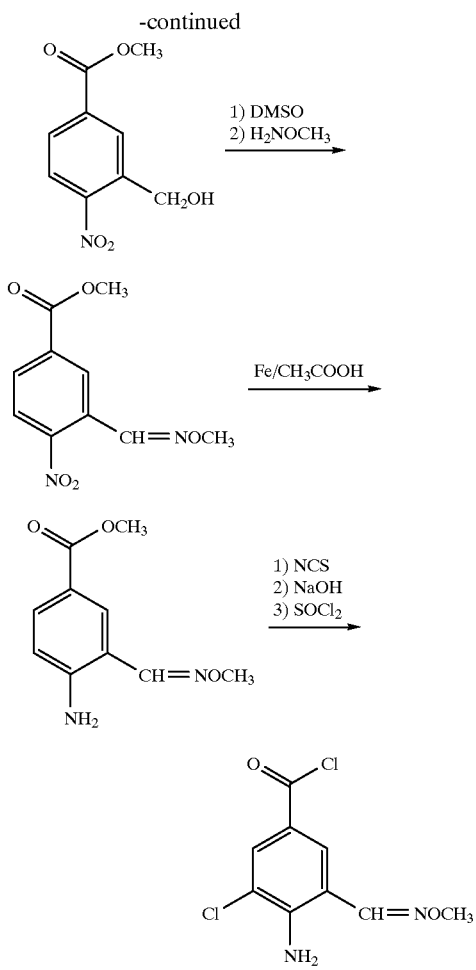

Other starting benzoyl chlorides may be obtained commercially or were prepared by the following procedure:

A mixture of benzoic acid (1.12 equivalents), thionyl chloride (1.71 equivalents), and dimethylformamide (catalytic amount), in toluene were slowly warmed to 70° C. and stirred at that temperature for 2 hours. The toluene was removed using a rotary evaporator to yield the desired acyl chloride, which was then used without further purification.

The compounds of the present invention are useful in controlling phytopathogenic fungi, particularly fungi of the class Oomycetes, and exhibit high fungicidal activity and relatively low phytotoxicity. The Oomycetes include organisms, e.g., those of the general Phytophthora, Plasmopara, Peronospora and Pseudoperonospora, which cause diseases such as potato and tomato late blight, and downy mildew in grapes and other crops.

The compounds of the present invention are useful for the control of phytopathogenic fungi on crops and may be used as seed protectants, soil fungicides and/or foliar fungicides. As a seed protectant, a compound of the present invention is coated on seed at a dosage rate of about 0.5 grams (g) compound per 50 kg seed to about 500 g compound per 50 kg seed. As a soil fungicide, a compound of the present invention can be incorporated in the soil or applied to the surface of the soil at a dosage rate of about 0.5 kg compound per hectare to about 20 kg compound per hectare and preferably at a rate of about 1 kg compound per hectare to about 5 kg compound per hectare.

The compounds of the present invention can be applied to plant foliage as fungicidal sprays by methods commonly employed, such as conventional high-gallonage hydraulic sprays, low-gallonage sprays, air-blast, aerial sprays and dusts. While the dilution and rate of application will depend upon the type of equipment employed, the method and frequency of application desired and diseases to be controlled, the effective amount is typically from about 0.01 kilogram (kg) compound per hectare to about 20 kg compound per hectare, preferably from about 0.1 kg compound per hectare to about 5 kg compound per hectare and more preferably from about 0.125 kg compound per hectare to about 0.5 kg compound per hectare.

For the above disclosed purposes these compounds can be used in the pure form, also known as technical in the art, as prepared, or as solutions or as formulations. The compounds are usually provided with a carrier or are formulated so as to render them suitable for subsequent use as fungicides. For example, the compounds can be formulated as wettable powders, dry powders, emulsifiable concentrates, dusts, granular formulations, aerosols, or flowable emulsion concentrates. In such formulations, the compounds are extended with a liquid or solid carrier and, when dried, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in McCutcheon's Emulsifiers and Detergents, McCutcheon's Emulsifiers and Detergents/Functional Materials and McCutcheon's Functional Materials all published annually by McCutcheon Division of MC Publishing Company (N.J.).

In general, the compounds utilized in this invention can be dissolved in appropriate solvents such as acetone, methanol, ethanol, dimethylformamide or dimethyl sulfoxide and such solutions extended with water. The concentrations of the solution can vary from 1% to 90% with a preferred range being 5% to 50%.

For the preparation of emulsifiable concentrates, the compounds used in the invention can be dissolved in suitable organic solvents or a mixture of solvents, together with an emulsifying agent which permits dispersion of the fungicide in water. The concentration of the active ingredient in emulsifiable concentrates is usually 10% to 90% and in flowable emulsion concentrates, this can be as high as 75%. Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%.

Dusts are prepared by mixing the compounds of the present invention salts and complexes thereof with finely divided inert solids which can be organic or inorganic in nature. Inert materials useful for this purpose include botanical flours, silicas, silicates, carbonates and clays. One convenient method of preparing a dust is to dilute a wettable powder with a finely divided carrier. Dust concentrations containing 20% to 80% of the active ingredient are commonly made and are subsequently diluted to 1% to 10% use concentration.

The compounds of the present invention can also be utilized in combination with other fungicides such as, for example, those disclosed in U.S. Pat. No. 5,304,572 (columns 3 and 4) as well as acylalanines such as, furalaxyl, cyprofuram, ofurace, benalaxyl, and oxadixyl; fluazinam, flumetover, phenylbenzamide derivatives such as those disclosed in EP 578586 A1, amino acid derivates such as valine derivatives disclosed in EP 550788 A1, methoxyacrylates such as methyl (E)-2-(2-(6-(2-cyanophenoxy)pyrimidin-4-yloxy)phenyl)-3-methoxyacrylate; benzo(1,2,3)thiadiazole-7-carbthioic acid s-methyl ester, propamocarb; imazalil; carbendazim; myclobutanil; fenbuconazole; tridemorph; pyrazophos; fenarimol; fenpiclonil; pyrimethanil; and tin fungicides. Those skilled in the art will recognize that mixtures of the respective compositions and compounds of the present invention with other fungicidally active compounds may provide advantages such as a broader spectrum of antifungal activity than the respective compositions and compounds of the present invention alone.

In a similar manner, the compositions and compounds of this invention may be applied in combination with one or more insecticides such as those disclosed in U.S. Pat. No. 5,075,471 (columns 14 and 15). Again, those skilled in the art will recognize that mixtures of the respective compositions and compounds of the present invention with insecticidally active compounds may provide advantages such as fewer total applications than if the fungicides and insecticides are applied separately.

EXAMPLES 1–3

In a three-necked, round-bottomed flask fitted with a mechanical stirrer, nitrogen inlet and thermometer were placed 4 grams (g) (0.03 mole) of 3-amino-3-methyl-1-pentyne hydrochloride (4 grams (g) (0.03 mole) suspended in 100 milliliters (mL) of methylene chloride in a three-necked, round-bottomed flask fitted with a mechanical stirrer, nitrogen inlet and thermometer. Triethylamine (6.82 g, 9.4 mL) was added slowly, keeping the temperature between 5° C. and 10° C. 4-nitrobenzoyl chloride 5 g (0.027 mole) was added to the resulting mixture at a rate to keep the reaction temperature between 5° C. and 10° C. After the addition was complete the reaction mixture was stirred at room temperature for 0.5 hours, and was then sequentially washed with water (2×100 mL), 5% aqueous hydrochloric acid, (2×100 mL), water (1×50 mL), 5% aqueous sodium hydroxide (2×100 mL) and finally with water (1×100 mL) before being dried over anhydrous magnesium sulfate. The solvent was removed in the rotary evaporator, yielding N-(3-methylpent-1-yn-3-yl)-4-nitrobenzamide, used as such in the next step.

In a 500 mL, three-necked, round-bottomed flask fitted with a mechanical stirrer, thermometer and addition funnel were placed 6.7 grams of the previously prepared N-(3-methylpent-1-yn-3-yl)-4-nitrobenzamide and 120 mL of methylene chloride. The resulting mixture was cooled down to −50° C. and then 26.2 mL (1.03 molar (M), 27 millimoles (mmole) of a cold chlorine solution in methylene chloride was added very slowly. When the addition was complete, the reaction mixture was stirred at −50° C. for 30 minutes. The solvent was then removed from the crude reaction mixture using a rotary evaporator, yielding a mixture of 2-(4-nitrophenyl)-4-ethyl-4methyl-5-chloromethylenyloxazoline hydrochloride and 2-(4-nitrophenyl)-4-ethyl-4-methyl-5-chloro-5-dichloromethyloxazoline hydrochloride which was used as such in the next step.

The oxazoline hydrochloride prepared in the preceding step was dissolved in a mixture of 85 mL of methanol, 42.5 mL of water and 4.25 mL of concentrated hydrochloric acid, warmed to 55° C. and then stirred at that temperature for four hours. The crude reaction mixture was then cooled and poured into 400 mL of cold water and extracted with methylene chloride (3×200 mL). The combined organic layers were then washed with water (2×250 mL) and dried over anhydrous magnesium sulfate. The solvent was then removed from the mixture using a rotary evaporator, yielding a mixture of N-(3-chloro-1-ethyl-1-methyl-2-oxopropyl)-4-nitrobenzamide and N-(3,3-dichloro-1-ethyl-1-methyl-2-oxopropyl)-4-nitrobenzamide which was used as such in the next step.

The mixture prepared in the previous step, 70 mL of ethanol and 150 mg of 5% palladium over charcoal were placed in a hydrogenation bottle and hydrogenated in a Parr apparatus (50 pounds per square inch, absolute (psia) at room temperature) for 1 hour. The reaction mixture was then filtered through celite and the solvent was removed under reduced pressure to yield the crude product. The product was separated by chromatographic column (silica gel, 1:1 ethyl acetate:hexane) yielded 290 mg of the desired N-(3-chloro-1-ethyl-1-methyl-2-oxopropyl)-4-aminobenzamide.

Using essentially the same procedure the following N-acetonylbenzamides of Formula (VI) were prepared:

Example 2 (N-(3-chloro-1-ethyl-1-methyl-2-oxopropyl)-3-aminobenzamide); and Example 3 (N-(3-chloro-1-ethyl-1-methyl-2-oxopropyl)-4-amino-3,5-dimethylbenzamide) were prepared using essentially the same procedure as set forth above in Example 1.

EXAMPLES 4–7

In a three-necked, round-bottomed flask fitted with a methanical stirrer, a nitrogen inlet and thermometer were placed 6.8 g, (0.051 mole) of 3-amino-3-methyl-1-pentyne hydrochloride 6.8 g, (0.051 mole) was suspended in 300 mL of methylene chloride in a three-necked, round-bottomed flask fitted with a mechanical stirrer, a nitrogen inlet and thermometer. Triethylamine 13.1 g (18 mL) was added slowly to the flask, keeping the temperature between 5° C. and 10° C. To the resulting mixture, 4-amino-3,5-dibromobenzoyl chloride 16 g (0.051 mole) was added at a rate to keep the reaction temperature between 5° C. and 10° C. After the addition was complete, the reaction mixture was stirred at room temperature for 0.5 hours, was then washed sequentially with water (2×150 mL), saturated aqueous ammonium chloride, (2×100 mL), water, (1×150 mL) and finally with 5% aqueous sodium hydroxide (1×100 mL) and was then dried over anhydrous magnesium sulfate. The crude product was redissolved in 250 mL of methylene chloride and then filtered through a small column containing a mixture of magnesium sulfate and silica gel. The solvent removed from the filtered product using a rotary evaporator to yield 10.8 g N-(3'-methylpent-1'-yn-3'-yl)-4-amino-3,5-dibromobenzamide.

In a 1000 mL, three-necked, round-bottomed flask fitted with a mechanical stirrer, a thermometer and addition funnel. The resulting mixture was cooled down to −50° C. and 35.4 mL (0.82M, 29 mmole) of a cold chlorine solution in methylene chloride was added very slowly. When the addition was complete, the reaction mixture was stirred at −50° C. for 30 minutes. The solvent was then removed from the crude reaction mixture using a rotary evaporator, yielding 2-(4-amino-3,5-dibromophenyl)-4-methyl-5-chloromethylenyloxazoline hydrochloride.

The oxazoline hydrochloride prepared in the preceding step was dissolved in a mixture of 116 mL of tetrahydrofuran, 14.5 mL of water, and 3.2 mL of concentrated sulfuric acid, warmed up to 55° C. and then stirred at that temperature overnight. The crude reaction mixture was then cooled down and poured into 250 mL of cold water and extracted with methylene chloride (3×150 mL). The combined organic layers were washed with water (2×100 mL) and then dried over anhydrous magnesium sulfate. The solvent was removed using a rotary evaporator to yield 8.8 g of crude product. The crude product was recrystallized from ethyl acetate:hexane, yielding 5.87 g of N-(3-chloro-1-ethyl-1-methyl-2-oxopropyl)-4-amino-3,5-dibromobenzamide.

The compounds of Example 5 (N-(3-chloro-1-ethyl-1-methyl-2-oxopropyl)-4-amino-3,5-diiodobenzamide); and Example 6 (N-(3-chloro-1-ethyl-1-methyl-2-oxopropyl)-4-amino-3,5-dichlorobenzamide) were prepared using essentially the same procedure as set forth above in Example 4.

The compound of Example 7 (N-(3,3-dichloro-1-ethyl-1-methyl-2-oxopropyl)-4-amino-3,5-dichlorobenzamide) was isolated as an impurity of the compound of Example 6.

EXAMPLE 8

In a 1000 mL, three-necked, round-bottomed flask fitted with a mechanical stirrer, nitrogen inlet and thermometer were placed 10 g of 4-acetamido-3-nitrobenzoic acid, 200 mL of tetrahydrofuran and 31 mL of triethylamine. The resulting well-stirred mixture was cooled to −30° C. and 3.9 mL of methane sulfonyl chloride were added dropwise while keeping the reaction temperature at −30° C. The resulting suspension was stirred at −30° C. for 30 minutes, after which 6.7 g of 3-amino-3-methyl-1-pentyne hydrochloride were added slowly over a 20 minute period. After the addition was complete, the reaction mixture was stirred at −30° C. for an additional 30 minutes. The reaction mixture was then poured into a mixture of 400 mL water and 200 mL of ethyl acetate. The phases were separated and the aqueous layer was then extracted with ethyl acetate (2×150 mL). The combined organic phases were washed sequentially with water (1×200 mL), 5% aqueous hydrochloric acid (2×200 mL), water (1×200 mL), 2% aqueous sodium hydroxide (2×200 mL) and water (1×200 mL) and then dried over anhydrous magnesium sulfate. The solvent was removed in the rotary evaporator, yielding 8.2 g of N-(3-methylpent-1-yn-3-yl)-4-acetamido-3-nitrobenzamide.

In a 500 mL, three-necked, round-bottomed flask fitted with a mechanical stirrer, a thermometer and addition funnel, the N-(3-methylpent-1-yn-3-yl)-4-acetamido-3-nitrobenzaide preapared in the preceeding step was dissolved in 180 mL of methylene chloride. The resulting mixture was cooled to −50° C. and 26.2 mL (1.03M, 27 mmole) of a cold chlorine solution in methylene chloride was added very slowly. When the addition was complete, the reaction mixture was stirred at −50° C. for 30 minutes. The solvent was then removed from the crude reaction mixture using a rotary evaporator, yielding 9.07 of 2-(4-acetamido-3-nitrophenyl)-4-ethyl-4-methyl-5-chloromethylenyloxazoline hydrochloride.

The oxazoline hydrochloride (7.3 g) prepared in the preceding step was dissolved in a mixture of 78 mL of tetrahydrofuran, 9.75 mL of water, and 2.1 mL of concentrated sulfuric acid, heated to 55° C. and stirred at that temperature overnight. The crude reaction mixture was cooled and poured into cold water and then extracted with methylene chloride (3×150 mL). The combined organic layers were washed with water (2×100 mL) and then dried over anhydrous magnesium sulfate. The solvent was then removed using a rotary evaporator, yielding an amber crystalline solid which was titrated with hexane, yielding 5.3 g of crude product. The crude product was dissolved in a 1:1 mixture of ethyl acetate and hexane and the solution was passed through a chromatographic column (200–400 mesh Silica gel using a 1:1 ethyl acetate:hexane as solvent), yielding 1.4 g of N-(3-chloro-1-ethyl-1-methyl-2-oxopropyl)-4-amino-3-nitrobenzamide.

EXAMPLE 9

In a 500 mL, three-necked, round-bottomed flask fitted with a mechanical stirrer, nitrogen inlet and thermometer were placed 10 g of 3-methyl-4-nitrobenzoic acid, 200 mL of tetrahydrofuran and 38 mL triethylamine were added to The resulting well-stirred mixture was cooled to −30° C. and 4.7 mL of methane sulfonyl chloride were added dropwise keeping the reaction temperature at −30° C. The resulting suspension was stirred at −30° C. during 30 minutes, after which 8.1 g of 3-amino-3-methyl-1-pentyne hydrochloride were added slowly over a 20 minute period. After the addition was complete the reaction mixture was stirred at −30° C. for an additional 30 minutes. The reaction mixture was then poured into a mixture of 400 mL water and 200 mL of ethyl acetate. The phases were separated and the aqueous layer was extracted with ethyl acetate (2×150 mL). The combined organic phases were washed sequentially with water (1×200 mL), 5% aqueous hydrochloric acid (2×200 mL), water (1×200 mL), 5% aqueous sodium hydroxide (2×200 mL) and finally with water (1×200 mL) and then dried over anhydrous magnesium sulfate. The solvent was removed using a rotary evaporator, yielding the crude product. The crude product was dissolved in 100 mL of methylene chloride and filtered through a small silica gel column yielding 4.11 g of N-(3-methylpent-1-yn-3-yl)-3-methyl-4-nitrobenzamide.

In a 500 mL, three-necked, round-bottomed flask fitted with a mechanical stirrer, a thermometer and addition funnel, 4.1 g of the N-(3-methylpent-1-yn-3-yl)-3-methyl-4-nitrobenzamide prepared in the preceding step was dissolved in 100 mL of methylene chloride. The resulting mixture was cooled down to −50° C. and 19.3 mL (0.82M, 16 mmole) of a cold chlorine solution in methylene chloride were added very slowly. When the addition was complete, the reaction mixture was stirred at −50° C. for 30 minutes. The solvent was removed from the crude reaction mixture using a rotary evaporator, yielding 5.29 g 2-(3-methyl-4-nitrophenyl)-4-ethyl-4-methyl-5-chloromethylenyloxazoline hydrochloride.

The oxazoline hydrochloride prepared in the preceding step was dissolved in 52 mL of methanol, 10 mL of water, and 2.6 mL of concentrated hydrochloric acid, heated to 55° C. and stirred for 4 hours. The crude reaction mixture was cooled and poured into 400 mL of cold water and then extracted with methylene chloride (3×150 mL). The combined organic layers were washed with water (2×200 mL) and then dried over anhydrous magnesium sulfate. The solvent was removed using a rotary evaporator, yielding 2.1 g N-(3-chloro-1-ethyl-1-methyl-2-oxopropyl)-3-methyl-4-nitrobenzamide as a light yellow crystalline solid.

The N-(3-chloro-1-ethyl-1-methyl-2-oxopropyl)-3-methyl-4-nitrobenzamide (2 g) prepared in the previous step, 70 mL of ethanol and 150 mg of 5% palladium over charcoal were placed in a hydrogenation bottle and hydrogenated in a Parr apparatus (50 psia, room temperature) for 3 hours. The reaction mixture was then filtered through celite and the solvent eliminated under reduced pressure yield to the crude product. Separation of the crude product by chromatographic column (1:1 ethyl acetate:hexane) yielded 50 mg of the expected N-(3-chloro-1-ethyl-1-methyl-2-oxopropyl)-4-amino-3-methylbenzamide.

EXAMPLE 10

In a 125 mL, three-necked, round-bottomed flask fitted with a mechanical stirrer nitrogen inlet and thermometer were placed 13.4 g (0.1 mole) of 3-methyl-1-pentyn-3-amine hydrochloride, 45 mL dimethylformamide and cooled down to 0° C. To the resulting well-stirred mixture was added slowly 20.2 g (0.2 mole) of triethylamine dropwise, keeping the temperature below 3° C. After the addition was completed, the reaction mixture was stirred 15 minutes followed by dropwise addition of 18.9 g (0.09 mole) of trifluoroacetic anhydride dissolved in 35 mL of tetrahydrofuran at such a rate to keep the reaction temperature below 3° C. After the addition was completed, the reaction mixture was stirred at room temperature overnight and then poured into a mixture of 100 mL of water and 100 mL of ethyl ether. The lower phase was discarded, the organic layer was washed sequentially with saturated aqueous sodium bicarbonate and brine, dried over anhydrous magnesium sulfate, treated with activated charcoal and then filtered through celite. The solvent was then eliminated under reduced pressure, yielding 12.1 g (70% yield) N-[3-(3-methyl-1-pentynyl)]trifluoroacetamide as a white solid.

The above described reaction was repeated using 231 g (1.1 mole) of trifluoroacetic anhydride, 163 g (1.2 mole) of 3-methyl-1-pentyn-3-amine hydrochloride, 247 g (2.4 mole) of triethylamine, 500 mL tetrahydrofuran and 500 mL of dimethylformamide, yielding 168.3 g N-[3-(3-methyl-1-pentynyl)]trifluoroacetamide.

In a 1 L, three-necked, round-bottomed flask fitted with a mechanical stirrer, a thermometer and a 100 mL addition funnel, 11.4 g, (59 mole) of N-[3-3-methyl-1-pentynyl)]trifluoroacetamide was dissolved in 200 mL of methylene chloride. The resulting mixture was cooled to −30° C and a 10.7 g of chlorine were bubbled in over a 0.5 hour period. When the addition was completed the reaction mixture was stirred at −30° C. for 30 minutes, then warmed to room temperature and stirred for 3 hours. The solvent was then removed from the crude reaction mixture using a rotary evaporator, yielding 2-trifluoromethyl-4-methyl-4-ethyl-5-chloro-5-(dichloromethyl)-oxazoline hydrochloride, which was used as such in the next step.

The 2-trifluoromethyl-4-methyl-4-ethyl-5-chloro-5-(dichloromethyl)oxazoline hydrochloride prepared in the preceding step was dissolved in a mixture of 80 mL methanol, 3.2 mL of water, and 8.3 mL of concentrated hydrochloric acid, warmed to 50° C. and stirred at that temperature overnight. The crude reaction mixture was cooled and poured into ice/water/ethyl ether mixture. The organic phase was extracted once with water. The combined aqueous layers were washed once with ethyl ether, neutralized with saturated aqueous sodium bicarbonate and extracted with twice with ethyl ether. The combined ether layers were then washed with water, brine, dried over anhydrous magnesium sulfate, treated with activated charcoal and filtered through celite. Anhydrous hydrogen chloride was bubbled into the resulting clear solution. The resulting white solid was filtered and dried, yielding 8.1 g 3-amino-1,1-dichloro-3-methyl-2-pentanone hydrochloride as a white solid. This reaction was repeated using 168.3 g (0.87 mole) of N-[3-(3-methyl-1-pentynyl)] trifluoroacetamide, 155 g (2.2 mole) of chlorine followed by acid hydrolysis to yield 99.7 g (52%) 3-amino-1,1-dichloro-3-methyl-2-pentanone hydrochloride ($^{1}$H-NMR, (DMSO-$d_6$) 8.95(3,bs); 7.55(1,s); 2.25–1.85(2,m); 1.65(3,s); 0.85(3,t)).

In a 2 L Parr bottle were placed 41 g of 3-amino-1,1-dichloro-3-methyl-2-pentanone hydrochloride, 0.8 g of 10% palladium over charcoal and 400 ml of ethanol (200 proof). The resulting mixture was shaken in a Parr apparatus at 50 psi for 3 hours. The crude reaction mixture was filtered through Celite™ filter agent and evaporated in vacuo. A viscous oil resulted, which was taken up in approximately 400 ml of ethyl acetate and stirred at room temperature for several hours. The expected 3-amino-1-chloro-3-methyl-2-pentanone hydrochloride crystallized as a white solid. To the resulting suspension were added 300 ml of hexane. Filtration yielded 34 g (98%) of the expected 3-amino-1-chloro-3-methyl-2-pentanone hydrochloride (Compound 14).

In a 250 mL three-necked, round-bottomed flask fitted with a mechanical stirrer nitrogen inlet and thermometer were placed 3 g of 4-diethylaminobenzoic acid, 60 mL of tetrahydrofuran and 6.4 g of triethylamine. To the resulting well-stirred mixture was added 1.3 mL methane sulfonyl chloride dropwise while keeping the reaction temperature at −30° C. The resulting suspension was stirred at −30° C. for 15 minutes, after which 3.76 g of 3-amino-1,1-dichloro-3-methyl-2-pentanone hydrochloride were added slowly over a 60 minute period. After the addition was completed, the reaction mixture was stirred at −30° C. for an additional 45 minutes. The reaction mixture was poured into a mixture of 200 mL of water and 100 mL of ethyl acetate. The phases were separated and the aqueous layer was extracted with ethyl acetate (2×60 mL). The combined organic phases were washed sequentially with water (1×60 mL), 3% aqueous hydrochloric acid (2×100 mL), brine (1×100 mL) and 3% aqueous sodium hydroxide (2×100 mL), and then dried over anhydrous magnesium sulfate. The solvent then was removed using a rotary evaporator, yielding 410 mg N-(3,3-dichloro-1-ethyl-1-methyl-2-oxopropyl)-4-diethylaminobenzamide.

The N-(3,3-dichloro-1-ethyl-1-methyl-2-oxopropyl)-4-diethylaminobenzamide (390 mg) prepared in the previous step, 50 mL of ethanol and 75 mg of 5% palladium over charcoal were placed in a hydrogenation bottle and hydrogenated in a Parr apparatus (50 psia, room temperature) for 3 hours. The reaction mixture was filtered through celite and the solvent eliminated under reduced pressure, to yield a crude product. The crude product was dissolved in ethyl acetate and then shaken with saturated aqueous sodium bicarbonate. The phases were separated and the organic layer was dried over anhydrous magnesium sulfate. The solvent was then eliminated using a rotary evaporator, yielding 270 mg N-(3-chloro-1-ethyl-1-methyl-2-oxopropyl)-4-diethylamino-benzamide.

EXAMPLE 11

In a 300 mL three-necked, round-bottomed flask were dissolved 5.2 g (34.4 mmole) of 4-amino-3-methylbenzoic acid in 75 ml of anhydrous methanol. Anhydrous hydrogen chloride was bubbled into the flask for 3 to 5 minutes and the resulting solution was refluxed for 2 hours. The solvent was removed using a rotary evaporator, the resulting residue was introduced into a mixture of 200 ml of water and 100 ml of methylene chloride and the mixture was then separated into two phases. The aqueous layer was made basic with 10% aqueous sodium hydroxide and extracted with methylene chloride (3×100 ml). The combined organic layers were dried over anhydrous magnesium sulfate and the solvent removed using a rotary evaporator yielding 5.68 g methyl 4-amino-3-methylbenzoate.

In a 300 mL three-necked, round-bottomed flask fitted with a magnetic stirrer, condenser equipped with nitrogen inlet, and thermometer were placed 5.68 (25 mmole) of methyl 4-amino-3-methylbenzoate and 35 mL of acetonitrile. The flask was immersed in a preheated oil bath (oil bath temperature 70° C.) and 5.15 g (37.8 mmole) of N-chlorosuccinimide was added all at once. The resulting mixture was refluxed for 2 hours then cooled to room temperature to stand overnight. The reaction mixture was concentrated by removing solvent using a rotary evaporator and the resulting residue was partitioned between a mixture of 100 ml of ethyl ether and 100 ml of water. The organic layer was dried over anhydrous magnesium sulfate and the solvent was removed using a rotary evaporator, yielding 6.05 g methyl 4-amino-3-chloro-5-methylbenzoate.

In a 100 ml round-bottomed flask fitted with a magnetic stirrer, were placed 5 g (25 mmole) of methyl 4-amino-3-chloro-5-methylbenzoate and 10 mL of chloroform. The solution was stirred at room temperature and a solution of 2.31 ml (32.5 mmole) of acetyl chloride in 5 ml of chloroform was added dropwise using a syringe. A precipitate formed almost immediately. A condenser was then attached to the reaction vessel and the reaction mixture was warmed up to a gentle reflux for 75 minutes. The reaction mixture was concentrated to dryness using a rotary evaporator. The resulting solid was recrystallized from a mixture of 35 ml of methylene chloride and 10 ml of hexane yielding 3.25 g methyl 4-acetamido-3-chloro-5-methylbenzoate.

To a cooled solution (ice bath) of 10.8 g of methyl 4-acetamido-3-chloro-5-methylbenzoate in 73.8 ml of glacial acetic acid; and 73.8 ml of acetic anhydride were added dropwise 11 mL of concentrated sulfuric acid followed by the portion wise addition of 12.96 g (0.1295 mole) of chromium trioxide over a 25 minute period. The reaction mixture was stirred at 0° C. for 2.5 hours and then poured into a mixture of 612 g of ice and 162 ml of water. The resulting aqueous mixture was extracted with methylene chloride (4×250 ml). The combined organic layers were washed sequentially with water (3×250 ml), 5% aqueous sodium bicarbonate (2×250 ml) and then brine (1×250 ml) and dried over anhydrous magnesium sulfate. The solvent was removed in a rotary evaporator. The resulting residue was purified by chromatographic column (silica gel, ethyl acetate:hexane 30:70 followed by ethyl acetate:hexane 50:50), yielding 2.5 g methyl 4-acetamido-3-chloro-5-formylbenzoate.

To a cooled solution (ice bath) of 2.6 g (10.15 mmole) of methyl 4-acetamido-3-chloro-5-formylbenzoate in 75 ml of methylene chloride was added 1.16 g (13.87 mmole) of methoxylamine hydrochloride followed by 1.93 mL (13.87 mmole) of triethylamine. The ice bath was removed and the resulting mixture stirred overnight at room temperature. The reaction mixture was then washed with water and dried over anhydrous magnesium sulfate. The solvent was removed using a rotary evaporator, yielding 2.29 g methyl 4-acetamido-3-chloro-5-methoxyimino-methylbenzoate used without further purification in the next step.

The preceding methyl 4-acetamido-3-chloro-5-methoxyiminomethylbenzoate was dissolved in a mixture of 83 ml of methanol and 27.6 ml of 1.2N aqueous hydrochloric acid and the solution was refluxed overnight. The mixture was concentrated using a rotary evaporator and then partitioned between ethyl acetate and water. The aqueous phase was extracted with ethyl acetate and the combined organic layers were washed with water and dried over anhydrous magnesium sulfate. The solvent was then removed using a rotary evaporator, yielding 2.7 g methyl 4-amino-3-chloro-5-methoxyimino-methylbenzoate.

The methyl 4-amino-3-chloro-5-methoxyiminomethylbenzoate made in the previous step was dissolved in a mixture of 25 ml of methanol and 8 g ml of 10% of aqueous sodium hydroxide and the solution was then was refluxed for 2 hours. The methanol was removed using a rotary evaporator and the residue was partitioned between 25 ml of water and 25 ml of methylene chloride. To the cooled aqueous layer was added 6N aqueous hydrochloric acid, dropwise, with stirring, until the pH of mixture reached a value of 1. The resulting solid was filtered and dried yielding 1.4 g 4-amino-3-chloro-5-methoxyiminomethylbenzoic acid used without further purification.

In a 100 ml, three-necked, round-bottomed flask fitted with a mechanical stirrer, nitrogen inlet and thermometer were placed 1.27 g (5.5 mmole) of the preceding 4-amino-3-chloro-5-methoxyiminomethylbenzoic acid, (25 ml of tetrahydrofuran and 2.31 ml (16.6 mmole) of triethylamine. The resulting well-stirred mixture was cooled to −30° C. and 0.47 ml (6.1 mmole) of methane sulfonyl chloride were added dropwise keeping the reaction temperature at −30° C. The resulting suspension was stirred at −30° C. during 30 minutes, after which 0.74 g (5.5 mmole) of 3-amino-3-methyl-1-pentyne hydrochloride were added over a 20 minute period. After the addition was completed, the reaction mixture was stirred at −30° C. for an additional 30 minutes. The reaction mixture was poured into water and extracted with methylene chloride (3×25 ml). The combined organic phases were washed sequentially with water (1×20 ml), 5% aqueous hydrochloric acid (2×20 ml), water (1×20 ml), 2% aqueous sodium hydroxide (2×20 ml) and then with water (1×20 ml) and dried over anhydrous magnesium sulfate. The solvent was removed using a rotary evaporator, yielding 1.05 g of the expected N-(3-methylpent-1-yn-3-yl)-4-amino-3-chloro-5-methoxyiminomethylbenzamide, used in the next step without further purification.

In a 100 ml, three-necked, round-bottomed flask fitted with a mechanical stirrer, a thermometer and addition funnel was dissolved the preceding N-(3-methylpent-1-yn-3-yl)-4-amino-3-chloro-5-methoxyiminomethyl-benzamide, in 56 mL of methylene chloride. The resulting mixture was cooled to −50° C. and 4.32 ml (0.79M, 3.4 mmole) of a cold chlorine dissolved in methylene chloride was added very slowly. When the addition was complete the reaction mixture was stirred at −50° C. for 30 minutes. The reaction mixture was allowed to warm to room temperature and stirred overnight. The solvent was removed from the crude reaction mixture using a rotary evaporator yielding 1.13 g of a crude mixture containing N-(3-chloro-1-ethyl-1-methyl-2-oxopropyl)-4-amino-3,5-diiodobenzamide.

The mixture obtained in the preceding step was dissolved in 12 ml of tetrahydrofuran, 1.5 ml of water, and 0.33 ml of concentrated sulfuric acid, heated to 55° C. and stirred for 4 hours. The crude reaction mixture was cooled, poured into cold water and extracted with methylene chloride (2×10 ml). The combined organic layers were washed with water (1×100 ml) and then dried over anhydrous magnesium sulfate. The solvent was removed using a rotary evaporator, yielding the crude product. The crude reaction mixture was purified using a chromatographic column (30:70 ethyl acetate:hexane), which yielded N-(3-chloro-1-ethyl-1-methyl-2-oxopropyl)-4-amino-3-chloro-5-methoxyiminomethylbenzamide.

Another synthetic route to N-(3-chloro-1-ethyl-1-methyl-2-oxopropyl)-4-amino-3-chloro-5-methoxyiminomethylbenzamide is described below.

a) Preparation of methyl 3-methyl-4-nitrobenzoate

In a 5-liter three-necked round-bottomed flask equipped with a reflux condenser, overhead stirrer and gas inlet, was placed 300 g of 3-methyl-4-nitrobenzoic acid and 3 l of methanol. To the resulting well-stirred solution was bubbled in 20.8 g of hydrogen chloride and the resulting mixture was refluxed for 3 hours. The reaction mixture was cooled to room temperature and allowed to stand overnight. The expected methyl 3-methyl-4-nitrobenzoate precipitated as light yellow crystals, which were collected by suction filtration yielding after drying 259.3 g. This solid was used as such in the next step.

b) Preparation of methyl 3-bromomethyl-4-nitrobenzoate

In a 5-liter three-necked round-bottomed flask equipped with a reflux condenser, overhead stirrer, addition funnel and nitrogen inlet, was placed 220 g of methyl 3-methyl-4-nitrobenzoate, 2 l of anhydrous carbon tetrachloride and 4 g of benzoyl peroxide. To the resulting solution, irradiated with a 275 watt UV light, was added 198 g of bromine dropwise over a period of 2 hours at reflux. After the addition was complete the reaction mixture was refluxed for an additional 60 hours. The reaction mixture was cooled to room temperature. The solid which formed was separated by suction filtration. This solid (159.1 g) consisted of the expected methyl 3-bromomethyl-4-nitrobenzoate with minor amounts of the starting material. The mother liquors together with another 220 g of methyl 3-methyl-4-nitrobenzoate and 4 g of benzoyl peroxide were returned to the flask and treated with 198 g of bromine as described above. After the addition was complete the reaction mixture was refluxed another 96 hours, cooled to room temperature and the resulting solid separated by filtration yielding another 252 g of methyl 3-bromomethyl-4-nitrobenzoate. The solids were combined yielding a total of 411.1 g of methyl 3-bromomethyl-4-nitrobenzoate with minor amounts of the starting methyl 3-methyl-4-nitrobenzoate and methyl 3-dibromomethyl-4-nitrobenzoate. This solid was used as such in the next step.

c) Preparation of methyl 3-acetoxymethyl-4-nitrobenzoate

In a 5-liter three-necked round-bottomed flask equipped with a reflux condenser, overhead stirrer and nitrogen inlet, was placed 411 g of the previously prepared methyl 3-bromomethyl-4-nitrobenzoate, 441 g of anhydrous potassium acetate and 2 l of glacial acetic acid. The resulting mixture was refluxed for 4 hours, cooled to room temperature and stirred overnight. The solvent was removed in a rotary evaporator and the resulting light yellow solid treated with a mixture of 2 l of ethyl acetate and 1 l of water. The organic phase was separated, washed with water (3×400 mL), brine (1×400 mL) dried over anhydrous magnesium sulfate and the solvent removed using a rotary evaporator. The crude reaction mixture was triturated with hexane and filtered yielding 318 g of the expected methyl 3-acetoxymethyl-4-nitrobenzoate. This compound was used as such in the next step.

d) Preparation of methyl 3-hydroxymethyl-4-nitrobenzoate

In a 5-liter three-necked round-bottomed flask equipped with a reflux condenser, overhead stirrer and nitrogen inlet, was placed 318 g of the previously prepared methyl 3-acetoxymethyl-4-nitrobenzoate and 3.2 l of anhydrous methanol. To the resulting solution was bubbled in 40 g of hydrogen chloride and the resulting mixture was refluxed for 3 hours. After cooling to room temperature the solvent was removed using a rotary evaporator yielding 273 g of methyl 3-hydroxymethyl-4-nitrobenzoate as a yellow solid containing traces of methanol, which was used as such in the next step.

e) Preparation of methyl 3-formyl-4-nitrobenzoate

In a 5-liter four-necked round-bottomed flask 1.5 l of methylene chloride was cooled to −78° C. Oxalyl chloride (164 g 1.29 moles) was added slowly, followed by dropwise addition of 202 g (2.59 moles) of dry dimethylsulfoxide in 125 mL of methylene chloride, keeping the temperature below −70° C. After the addition was complete the reaction mixture was stirred at −78° C. for 30 minutes and 273 g (1.29 moles) of previously prepared methyl 3-hydroxymethyl-4-nitrobenzoate dissolved in 250 mL of methylene chloride was added dropwise. The reaction mixture was stirred an additional 30 minutes. Triethylamine (392 g 3.88 moles) in 125 mL of methylene chloride was added dropwise keeping the temperature below −65° C. The reaction mixture was warmed up slowly to room temperature and stirred overnight. The solvent was removed using a rotary evaporator and the resulting solid treated with a mixture of 2 l of ethyl acetate and 1 l of water. The organic phase was separated, filtered through diatomaceous earth, and washed sequentially with dilute aqueous hydrochloric acid (2×250 mL), water (2×250 mL), saturated aqueous sodium bicarbonate (2×250 mL), water (2×200 mL), brine (1×200 mL) and dried over anhydrous magnesium sulfate. The solvent was removed using a rotary evaporator. The crude reaction mixture was triturated with hexane and filtered yielding 234.1 g of the expected methyl 3-formyl-4-nitrobenzoate as a yellow solid. This compound was used as such in the next step.

f) Preparation of methyl 3-methoxyiminomethyl-4-nitrobenzoate

To a well stirred mixture of 195 g of methyl 3-formyl-4-nitrobenzoate, 1 l methylene chloride and 370 mL of water was added sequentially 77.6 g of methoxylamine hydrochloride, 76.2 g of sodium acetate and 6.8 g of tetra-n-butylammonium hydrogen sulfate. The resulting mixture was stirred overnight at room temperature, then diluted with 2 l of ethyl ether. The organic phase was separated and washed sequentially with water (1×500 mL), 2% aqueous hydrochloric acid (2×500 mL), water (2×250 mL), and brine (1×250 mL); then dried over anhydrous magnesium sulfate. The solvent was removed using a rotary evaporator yielding 218.6 g the expected methyl 3-methoxyiminomethyl-4-nitrobenzoate as a reddish oil that solidified upon standing, and which was used as such in the next step.

g) Preparation of methyl 4-amino-3-methoxyiminomethylbenzoate

In a 5-liter three-necked round-bottomed flask was placed 0.9 l of 5% aqueous acetic acid and 157 g (2.8 moles) of iron. To the resulting well-stirred mixture was added 166.6 g (0.7 moles) of the previously prepared methyl 3-methoxyiminomethyl-4-nitrobenzoate dissolved in 0.9 l of ethyl acetate followed by dropwise addition of 0.9 l of acetic acid while keeping the temperature below 35° C. The resulting mixture was stirred at 35° C. for 30 minutes and filtered through diatomaceous earth. The filtrate was poured into 5 l of water. The aqueous phase was separated and washed with ethyl ether (2×500 mL). The combined organic layers were washed sequentially with water (4×500 mL), saturated aqueous sodium bicarbonate (2×500 mL), water (2×500 mL), and brine (1×400 mL). The organic layer was dried over anhydrous magnesium sulfate and the solvent removed using a rotary evaporator yielding 130 g of the expected methyl 4-amino-3-methoxyiminomethylbenzoate.

h) Preparation of methyl 4-amino-3-chloro-5-methoxyiminomethylbenzoate

In a 2-liter three-necked round-bottomed flask was placed 106 g (0.51 moles) of the previously prepared 4-amino-3-methoxyiminomethylbenzoate and 500 mL of acetonitrile. The resulting mixture was heated at 70° C. and 75.2 g (0.56 moles) of N-chlorosuccinimide was added portionwise while keeping the temperature below 80° C. After the addition was complete the reaction mixture was refluxed for 1 hour. The reaction mixture was cooled to room temperature and the solvent eliminated in a rotary evaporator. The crude product was dissolved in 5 l of ethyl acetate. The organic solution was washed with water (3×500 mL) and brine, then dried over magnesium sulfate. The reaction mixture was concentrated in a rotary evaporator to a slurry, triturated with hexane and filtered yielding the expected methyl 4-amino-3-chloro-5-methoxyiminomethylbenzoate as a yellow solid. This reaction was repeated using the same amounts yielding a total of 210.5 g of methyl 4-amino-3-chloro-5-methoxyiminomethylbenzoate, which was used as such in the next step.

i) Preparation of 4-amino-3-chloro-5-methoxyiminomethylbenzoic acid

In a 5-liter three-necked round-bottomed flask was placed 210 g (0.86 moles) of the previously prepared 4-amino-3-chloro-5-methoxyiminomethylbenzoate, 1.7 l of methanol and 462 g (1.73 moles) of 15% aqueous sodium hydroxide. The resulting mixture was refluxed for 3 hours, after which the reaction mixture was stirred overnight at room temperature. The reaction mixture was concentrated using a rotary evaporator. The crude reaction mixture was dissolved in 2 l of water. The resulting aqueous solution was washed once with 500 mL of ethyl acetate, cooled in an ice bath and acidified to pH=2 with concentrated hydrochloric acid. The expected 4-amino-3-chloro-5-methoxyiminomethylbenzoic acid precipitated as a light yellow solid which was separated by suction filtration. The filter cake was washed with a 1:2 mixture of ethyl ether and hexane yielding after drying 185.2 g (94% yield).

(i) Preparation of 4-amino-3-chloro-5-methoxyiminomethylbenzoyl chloride

In a 5-liter three-necked round-bottomed flask was placed 180 g of the previously prepared 4-amino-3-chloro-5-methoxyiminomethylbenzoic acid, 2 l of toluene, 3 mL of dimethylformamide and 104 g (64 mL) of thionyl chloride. The resulting mixture was heated at 70° C. for 2 hours, filtered while hot and the solvent removed using a rotary evaporator yielding 178.1 g of the expected 4-amino-3-chloro-5-methoxyiminomethylbenzoyl chloride.

(i) Preparation of 4-amino-3-chloro-5-methoxyiminomethyl-N-(3-chloro-1-ethyl-1-methyl-2-oxopropyl)benzamide In a 5-liter three-necked round bottomed flask was placed 93 g of 3-amino-1-chloro-3-methyl-2-pentanone hydrochloride and 885 mL of water. To the resulting solution were added 138.6 g of sodium bicarbonate followed by 500 mL of ethyl acetate. To the resulting well-stirred mixture was added 123.5 g of 4-amino-3-chloro-5-methoxyiminomethylbenzoyl chloride dissolved in 1000 mL of ethyl acetate at room temperature over a period of 50 minutes. After the addition was complete the reaction mixture was stirred at room temperature for 1 hour. The two phases were separated and the organic layer was washed with water (2×500 mL), brine (1×500 mL), dried over anhydrous magnesium sulfate and the solvent eliminated in a rotary evaporator yielding the crude product as a brown oil. This oil was passed through a short Silica Gel column using methylene chloride as elution solvent. Evaporation of the solvent yielded 133.3 g of the expected 4-amino-3-chloro-5-methoxyiminomethyl-N-(3-chloro-1-ethyl-1-methyl-2-oxopropyl)benzamide as an off-white solid (mp 140–141° C.).

EXAMPLES 12 AND 13

In a 300 mL, three-necked, round-bottomed flask fitted with a mechanical stirrer, nitrogen inlet and thermometer were placed 5 g (0.03 mole) of 6-amino-5-chloronicotinic acid, 150 mL of tetrahydrofuran and 6.67 g (0.066 mole) of triethylamine. The resulting well-stirred mixture was cooled to −30° C. and 2.24 ml (0.03 mole) of methane sulfonyl chloride were added dropwise keeping the reaction temperature at −30° C. The resulting suspension was stirred at −30° C. during 30 minutes, after which 4.01 g (0.03 mole) of 3-amino-3-methyl-1-pentyne hydrochloride were added slowly over a 20 minute period. After the addition was completed, the reaction mixture was stirred at −30° C. for an additional 30 minutes. The reaction mixture was poured into water and extracted with methylene chloride (3×450 ml). The combined organic phases were washed with water (1×200 ml), and dried over anhydrous magnesium sulfate. The solvent was removed using a rotary evaporator, yielding the crude product. After purification by chromatographic column (silica gel, 1:1 ethyl acetate:hexane), 3.25 g N-(3-methylpent-1-yn-3-yl)-6-amino-5-chloronicotinamide were obtained as a white solid.

In a 100 mL, three-necked, round-bottomed flask fitted with a mechanical stirrer, a thermometer and addition funnel 1 g (3.97 mmole) of the preceding N-(3- methylpent-1-yn-3-yl)-6-amino-5-chloronicotinamide was suspended in 70 ml of methylene chloride. The resulting mixture was cooled to −50° C. and anhydrous hydrogen chloride was bubbled into the mixture until everything went to solution. Then 4.8 ml (0.85M, 4.08 mmole) of a cold chlorine solution in methylene chloride was added very slowly by syringe. When the addition was completed, the reaction mixture was stirred at −50° C. for 30 minutes. The reaction mixture was allowed to warm to room temperature and the solvent was then removed from the crude reaction mixture using a rotary evaporator, yielding 1.55 g of a solid (2-(6-amino-5-chloronicotinam-3-yl)-4-ethyl-4-methyl-5-chloromethylenyloxazoline hydrochloride) used as such in the next step.

The preceding 1.55 g of 2-(6-amino-5-chloronicotinam-3-yl)-4-ethyl-4-methyl-5-chloromethylenyloxazoline hydrochloride was dissolved in 15.9 ml of tetrahydrofuran, 1.99 ml of water, and 0.44 ml of concentrated sulfuric acid. The solution was warmed to 55° C. and stirred at that temperature for 3 hours. The crude reaction mixture was cooled and poured into a mixture of 50 ml of water and 50 ml of ethyl acetate. The phases separated and the aqueous layer was extracted with ethyl acetate (2×25 ml). The combined organic layers were washed sequentially with saturated sodium bicarbonate (1×10 ml), water (2×10 ml) and then dried over anhydrous magnesium sulfate. The solvent was then removed using a rotary evaporator, yielding the crude product as an oil. Crystallization from a mixture of hexane and ethyl ether yielded 0.85 of the expected N-(3-chloro-1-ethyl-1-methyl-2-oxopropyl)-6-amino-5-chloronicotinamide.

The compound of Example 13 (N-(3-chloro-1-ethyl-1-methyl-2-oxopropyl)-6-amino-5-chloronicotinamide hydrochloride was prepared from compound 12 by dissolving the compound 12 in hydroxyethyl ether, bubbling in dry hydrogen chloride gas, filtering out and then drying the resultant precipitate.

The compositions of each of the respective compounds of Examples 1–13 are summarized below in TABLE 1.

TABLE 1

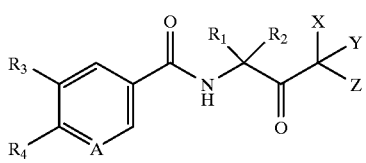

wherein: $R_1$ is $CH_3$; $R_2$ is $CH_2CH_3$; Z is Cl; Y is H and $R_3$, $R_4$ A and X are reported below.

| Example # | $R_3$ | $R_4$ | A | X |
|---|---|---|---|---|
| 1 | H | $NH_2$ | C—H | H |
| 2 | $NH_2$ | H | C—H | H |
| 3 | $CH_3$ | $NH_2$ | C—$CH_3$ | H |
| 4 | Br | $NH_2$ | CBr | H |
| 5 | Cl | $NH_2$ | C—Cl | H |
| 6 | Cl | $NH_2$ | C—Cl | CL |
| 7 | I | $NH_2$ | C—I | H |
| 8 | $NO_2$ | $NH_2$ | CH | H |
| 9 | $CH_3$ | $NH_2$ | CH | H |
| 10 | H | $N(CH_2CH_3)_2$ | CH | H |
| 11 | Cl | $NH_2$ | C—$CHNOCH_3$ | H |
| 12 | Cl | $NH_2$ | N | H |
| 13 | Cl | $NH_2$ | $NH^+Cl^-$ | H |

In addition, Coumpound 14 described the preparation described hereinabove, has the structure of Formula VIIa, where R1 is methyl and R2 is ethyl.

The nuclear magnetic resonance data for the compounds made in the above examples is presented below.

TABLE 2

| EX# | Solvent | $H^1$-NMR Data (200 MHz, delta scale in ppm, Tetramethylsilane (TMS) standard *) |
|---|---|---|
| 1 | Acet-D6 | 7.7(2, d); 6.7(2, d); 4.55(2, s); 2.3–1.8(2, m); 1.5(3, s); 0.9(3, t) |
| 2 | $CDCl_3$_ DMSO-d6 | 7.4(1, bs); 7.3–7.1(3, m); 6.85(1, d); 4.4(2, s); 2.1–1.9(2, m); 1.55(3, s); 0.9(3, t) |
| 3 | $CDCl_3$ | 7.4(2, s); 6.95(1, bs); 4.35(2, dd); 4.0(2, bs); 2.2(6, s); 2.3–1.8(2, m); 1.55(3, s); 0.9(3, t) |
| 4 | $CDCl_3$_ DMSO-d6 | 7.69(2, s); 7.0(1, bs); 4.95(2, bs); 4.48(2, dd); 2.3–1.8(2, m); 1.55(3, s); 0.89(3, t) |
| 5 | $CDCl_3$ | 7.65(2, s); 6.70(1, bs); 4.85(2, bs); 4.40(2, dd); 2.3–1.8(2, m)1.6(3, s); 0.9(3, t) |
| 6 | $CDCl_3$ | 7.75(2, s); 6.55(1, s); 6.45(1, bs); 4.9(2, bs); 2.3–1.8(2, m); 1.7(3, s); 0.9(3, t) |
| 7 | $CDCl_3$ | 8.05(2, s); 6.5(1, bs); 5.05(2, bs); 4.35(2, dd); 2.3–1.8(2, m); 1.57(3, s); 0.88(3, t) |
| 8 | $CDCl_3$_ DMSO-d6 | 8.75(1, s); 7.9(2, bs); 7.05(2, bs); 6.95(1, d); 4.4(2, s); 2.2–1.8(2, m); 1.5(3, s); 0.85(3, t) |
| 9 | $CDCl_3$ | 7.5(2, bs); 7.45(1, d); 6.75(1, s); 6.6(1, d); 4.45(2, dd); 2.15(3, s); 2.2–1.81(2, m); 1.5(3, s); 0.85(3, t) |
| 10 | $CDCl_3$ | 7.65(2, d); 6.65(2, d); 6.45(1, bs); 4.4(2, dd); 3.4(4, q); 2.2–1.8(2, m); 1.5(3, s); 1.2(6, t); 0.85(3, t) |
| 11 | $CDCl_3$ | 8.2(1, s); 7.7(1, s); 7.55(1, s); 6.55(2, bs); 4.40(2, dd); 3.95(3, s); 2.3–1.8(2, m); 1.6(3, s); 0.9(3, t) |
| 12 | $CDCl_3$ | 8.9(1, s); 8.4(1, s)7.9(1, s); 6.5(1, bs); 5.4(2, bs); 4.4(2, dd); 2.3–1.8(2, m); 1.6(3, s); 0.85(3, t) |
| 13 | $CDCl_3$ | 7.65(2, d); 6.65(2, d); 6.645(1, bs); 4.4(2, dd); 3.4(4, s); 2.2–1.8(2m); 1.5(3, s); 1.2(6, t); 0.85(3, t). |
| 14 | $CDCl_3$_ DMSO-d6 | 9.0(3, bs); 4.6–4.3(2, m); 2.3–1.8(2, m); 1.65(3, s); 1.0(3, t) |

* bs: broad singlet; d: doublet, dd: double of doublets, t: triplet, q: quartet, m: multriplet, s: singlet.

EXAMPLE 14

Compounds were tested for fungicidal activity against fungal diseases caused by *Phytophthora infestans, Botrytis cinerea, Pseudoperonospora cubensis, Plasmopara viticola, Piricularia oryzae* and *Erysiphe graminis* according to the procedures set forth below. Results are presented in Table 3.

Tomato Late Blight (TLB)

Spore suspensions, obtained from 1–2 week old *Phytophthora infestans* cultures grown on V8 juice agar, were used to inoculate tomato seedlings that were about two weeks old. An atomizer was used to apply the spores to the fungicide-treated foliage. The plants were kept in a humidity cabinet at 100% relative humidity for 24 hours, and then placed in a controlled temperature chamber for 5 days at 20° C. for disease development. Disease evaluations were recorded as "percent disease control", i.e., the relative efficacy of the test compound compared to no treatment, with 100% disease control indicating that the plants were observed to be disease free.

Botrytis Gray Mould on Tomato (BOT)

Several strains of *Botrytis cinerea* were maintained on potato dextrose agar for testing purposes. Spore suspensions of at least two strains were used to inoculate plants. A dextrose solution was used to wash the spores from sporulating cultures. The combined spore suspension was applied with an atomizer. Following inoculation the plants were placed in a controlled temperature chamber at 20° C. with 100% relative humidity for 5–7 days for disease development. Disease evaluations were recorded as percent disease control, according to the method described above for tomato late blight.

Cucumber Downy Mildew (CDM)

Cultures of *Pseudoperonospora cubensis* were maintained on Bush Champion cucumbers. Spore suspensions were obtained by washing infected leaves to obtain the inoculum. An atomizer was used to apply a suspension of spores to the lower leaves of the cucumbers. Following inoculation, the plants were kept in a humidity cabinet at 100% relative humidity for 24 hours and then placed in a controlled temperature chamber at 20° C. Disease evaluations were made seven days after inoculation and were recorded as percent disease control, according to the method described above for tomato late blight.

Grape Downy Mildew (GDM)

Cultures of *Plasmopara viticola* were maintained on grape seedlings derived from tissue culture. Leaves with sporulating mildew were rinsed in water to obtain the desired concentration of spores. An atomizer was used to apply a suspension of spores to the lower leaves of the grape plants. The plants were kept in a humidity cabinet at 100% relative humidity for 24 hours and then placed in a controlled temperature chamber at 20° C. for 7–8 days for disease development. Disease evaluations were recorded as percent disease control, according to the method described above for tomato late blight.

Rice Blast (RB)

*Piricularia oryzae* was maintained on potato dextrose agar for testing purposes. Spore suspensions were used to inoculate Nato rice plants by spraying the leaves and stems with an airbrush until a uniform film of inoculum was observed on the leaves. The inoculated plants were kept in a humidity cabinet at 100% relative humidity (75° F. to 85° F.) for 24 hours, then placed in a greenhouse environment for 7–8 days for disease development. Disease evaluations were recorded as percent disease control, according to the method described above for tomato late blight.

Wheat Powdery Mildew (WPM)

*Erysiphe graminis* (f. sp. tritici) was cultured on Pennol wheat seedlings in a controlled temperature room at 65° F.

to 75° F. Mildew spores were shaken from the culture plants onto Pennol wheat seedlings which had been sprayed previously with the fungicide compound. The inoculated seedlings were kept in a controlled temperature room at 65° F. to 75° F. for 8–10 days for disease development. Disease evaluations were recorded as percent disease control, according to the method described above for tomato late blight.

TABLE 3

EFFECTIVENESS OF TEST COMPOUNDS AGAINST FUNGAL DISEASES

| COMPOUND | Rate (ppm) | TLB | BOT | CDM | GDM | RB | WPM |
|---|---|---|---|---|---|---|---|
| 1 | 375 | 50 | — | — | — | — | 0 |
| 2 | 375 | 100 | — | — | — | — | 0 |
| 3 | 750 | 90 | — | — | — | — | 0 |
| 4 | 300 | 100 | 50 | 100 | 100 | 0 | 50 |
| 5 | 300 | 100 | 50 | 100 | 100 | 0 | 0 |
| 7 | 300 | 0 | 75 | — | 99 | 0 | 0 |
| 8 | 300 | 100 | 50 | 100 | — | 0 | 0 |
| 11 | 300 | 100 | 99 | 75 | — | 75 | 50 |
| 12 | 300 | 90 | 75 | — | 100 | 0 | 0 |
| 13 | 300 | 85 | 50 | — | 95 | 0 | 0 |

It has also been discovered that the acid salts of the Formula IX possess biocidal activity.

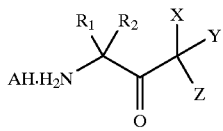

IX where HA is an organic or inorganic acid and $R_1$, $R_2$, X, Y and Z have the same meaning as in formula 1 described herein.

Especially preferred is when $R_1$ is methyl; $R_2$ is ethyl and Y is chloro, and X and Z are hydrogen.

The term organic or inorganic acid includes but is not limited to HCl, $H_2SO_4$, $HSO_3$, $HClO_4$, HBr. Especially preferred as the acid are strong acids such as HCl and $H_2SO_4$.

The acid salts of the present invention are readily prepared by the process shown below.

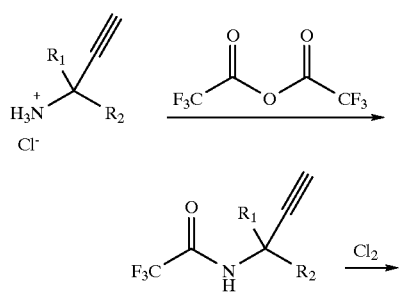

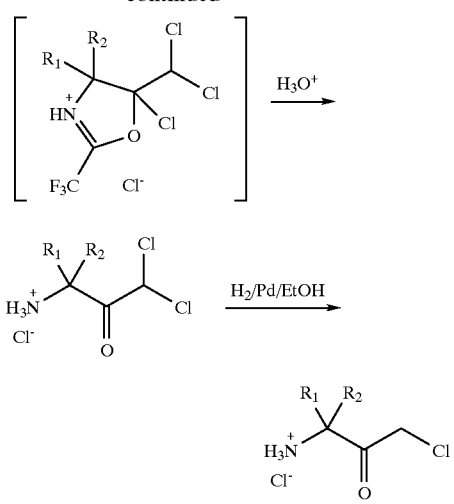

The acid salt compounds described above are effective in the control of a living organism in accordance with the invention by contacting the organism with the acid salt compound in an amount effective to control said organism. Any technique known in the art can be employed to disseminate the acid salt compound in a manner so as to achieve the desired contact with the organism to be controlled. Spraying and fumigating are typical of such techniques.

In general, a locus subject to contamination by microorganisms can be protected by incorporating into the locus the acid salt in an amount effective to control said microorganism. Contamination is meant to include any attack by microorganisms which leads to chemical or physical breakdown or disintegration of the locus as well as the growth of the microorganisms within the locus with or without an accompanying deleterious effect. The level of acid salt required will vary with the medium being protected, the microorganisms being controlled and the particular acid salt compounds being employed. Typically in a liquid medium excellent control is obtained when acid salts are incorporated in the range of 0.1 to 10,000 parts per million (ppm) or 0.00001 to 1% weight percent based on the weight of the medium.

As biocidally active compounds the acid salts are suitable for the control of living organisms. For this reason they are especially effective bactericidal, algicidal, fungicidal and slimicidal agents. As compounds which inhibit the growth of bacteria, fungi and algae the acid salts are placed in the location in which control is desired.

Typical uses for these compounds include any aqueous media, such as water cooling systems, swimming pools, paper pulp processes, aqueous polymer dispersions, water-based parts and the like. In addition these compounds and compositions containing the acid salts may be used as fabric and leather preservatives, cosmetic preservatives, soap additives, metal working fluids such as cutting oils and as preservatives for various materials such as fuels.

EXAMPLE 15

Antimicrobial Test Data

The spectrum of antimicrobial activity and the effect of anionic surfactant on the antimicrobial activity of Compound 14 of this invention were determined in minimum inhibitory concentration (MIC) tests. MICs were determined by two fold serial dilutions of Compound 14 in Minimal Salts Medium (M9G), Trypticase Soy Broth (TSB) or Trypticase Soy Broth and anionic surfactant (TSB+AOS). The test was performed using a stock solution or dispersion of the test compound, typically at a concentration of 1% by weight, made in dimethylsulfoxide. A volume of the stock solution was dispensed into culture media to give an initial starting test concentration of 500 parts per million (ppm) active ingredient.

In preparing two-fold serial dilutions of test compound, each vessel in the dilution series, except the first vessel, received an equal volume of compound free broth. The first vessel contained twice the volume of broth with the starting concentration of test compound. One half of the broth from the first vessel was transferred to the second vessel. After being mixed, one half of the resulting volume was removed from the second vessel and transferred to the third vessel. The entire cycle was repeated sufficiently to give a series of concentrations amounting to 500, 250, 125, 63, 31, 16, 8, 4, 2, 1, 0.5, 0.25 ppm active ingredient respectively.

Each vessel was then inoculated with a cell suspension of the appropriate test organism. Bacteria and fungi were grown on agar slants. Both were grown for a time and at a temperature appropriate to the species being tested. At the end of the growth period, slants were washed with phosphate buffer and cell suspensions were stored at 4° C. The cell/spore suspension was standardized by controlling incubation time, temperature, and the volume of the diluent. The suspension was then used to inoculate the vessels containing the various concentrations of Compound 14.

The vessels were then incubated at 30° C. for 48 hours. After the incubation, the vessels were examined for growth/no growth. The MIC is defined as the lowest concentration of compound that results in complete inhibition of growth of the test organism.

Compound 14 (Formula IX A=Cl, $R_1$=methyl, $R_2$=ethyl, Y=Cl and X=Z=H) was tested against *Aspergillus niger, Rhodotorula rubra, Escherichia coli,* and *Pseudomonas aeruginosa*. Results are provided in Table 4.

TABLE 4

Minimum Inhibitory Concentration (ppm)

| Compound | E. coli M9G | E. coli TSB | P. aeruginosa TSB | A. niger TSB | R. rubra TSB | E. coli TSB + AOS |
|---|---|---|---|---|---|---|
| 14 | 150 | 150 | 75 | 15 | >30 | 150 |

EXAMPLE 16

The fungicidal activity of Compound 14 against phytopathogenic fungi was tested according to the procedures set forth in Example 22 of U.S. Pat. No. 5,254,584. The results are provided in Table 5.

TABLE 5

Minimum Inhibitory Concentration (ppm)

| Compound | BOT | COL | HEL | PHY | PYR | PYT | RHI | SEP |
|---|---|---|---|---|---|---|---|---|
| 14 | >50 | >50 | 25 | 12 | 12 | 6 | 25 | 25 |

We claim:

1. A compound of the formula:

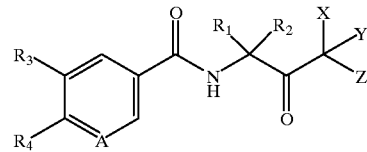

wherein:

A is N or C—$R_5$;

$R_1$ and $R_2$ are each independently H, ($C_1$–$C_6$)alkyl, halo($C_1$–$C_6$)alkyl, ($C_2$–$C_6$)alkenyl, or ($C_2$–$C_6$)alkynyl, provided that at least one of $R_1$ and $R_2$ is other than H;

$R_3$, $R_4$ and $R_5$ are each independently H, halo, cyano, ($C_1$–$C_6$)alkyl, halo($C_1$–$C_6$)alkyl, ($C_2$–$C_6$)alkenyl, ($C_2$–$C_6$)alkynyl, ($C_1$–$C_6$)alkoxyl, halo($C_1$–$C_6$)alkoxyl, nitro, carboxyl, —$NR_6R_7$, —$CR_8$=$NOR_9$, NHCOO$R_8$, or —CON$R_{10}R_{11}$, provided that at least one of $R_3$, $R_4$, and $R_5$ is —$NR_6R_7$;

$R_6$ and $R_7$ are each independently H, ($C_1$–$C_6$)alkyl, or ($C_1$–$C_6$)alkylcarbonyl;

$R_8$ is H, ($C_1$–$C_6$)alkyl, ($C_2$–$C_6$)alkenyl, ($C_2$–$C_6$)alkynyl, ($C_1$–$C_6$)alkylcarbonyl($C_1$–$C_4$)alkyl;

$R_9$ is H, ($C_1$–$C_6$)alkyl, ($C_2$–$C_6$)alkenyl, ($C_2$–$C_6$)alkynyl, or ($C_1$–$C_4$)alkylcarbonyl;

$R_{10}$ and $R_{11}$ are each independently H, ($C_1$–$C_6$)alkyl, ($C_2$–$C_6$)alkenyl, or ($C_2$–$C_6$)alkynyl;

X, Y and Z are each independently H, halo, cyano, thiocyano, isothiocyano or ($C_1$–$C_6$)alkylsulfonyloxy, provided that at least one of X, Y and Z is halo, cyano, thiocyano, isothiocyano, or ($C_1$–$C_6$)alkylsulfonyloxy;

and agronomically acceptable salts thereof.

2. The compound of claim 1 wherein A is C—$R_5$.

3. The compound of claim 2 wherein $R_1$ and $R_2$ are ($C_1$–$C_6$)alkyl.

4. The compound of claim 3 wherein $R_1$ is methyl and $R_2$ is ethyl.

5. The compound of claim 4 wherein $R_3$, $R_4$ and $R_5$ are each independently H, CH=NOCH$_3$, ($C_1$–$C_6$)alkyl, halo, nitro, cyano or —$NR_6R_7$, provided that at least one of $R_3$, $R_4$ and $R_5$ is $NR_6R_7$, and wherein $R_6$ and $R_7$ are each independently H or ($C_1$–$C_6$)alkyl.

6. The compound of claim 5 wherein $R_6$ and $R_7$ are each H.

7. The compound of claim 5 wherein X and Y are each H and Z is halo.

8. The compound of claim 5 wherein A is —$CR_5$, $R_1$ is methyl, $R_2$ is ethyl, $R_3$ and $R_5$ are each ($C_1$–$C_6$)alkyl, halo, CH=NOCH$_3$ or nitro, $R_4$ is NH$_2$, X and Y are each H and Z is chloro.

9. The compound of claim 1 wherein A is N, $R_1$ is methyl, $R_2$ is ethyl, $R_3$ is H, ($C_1$–$C_6$)alkyl, halo, CH=NOCH$_3$ or nitro, $R_4$ is NH$_2$, or CH=NOCH$_3$; X and Y are each H and Z is chloro.

10. A fungicidal composition, comprising an agronomically effective carrier and a fungicidally effective amount of the compound of claim 1.

11. A method for controlling phytopathogenic fungi, comprising applying a fungicidally effective amount of the compound of claim 1 to plant foliage, plant seed or to a growth medium.

* * * * *